(12) United States Patent
Okada et al.

(10) Patent No.: US 7,267,647 B2
(45) Date of Patent: Sep. 11, 2007

(54) ENDOSCOPE

(75) Inventors: Shinsuke Okada, Saitama-ken (JP); Peter Maxwell Delaney, Victoria (AU)

(73) Assignees: PENTAX Corporation, Tokyo (JP); Optiscan Pty Ltd., Victoria (AU)

(*) Notice: Subject to any disclaimer, the term of this patent is extended or adjusted under 35 U.S.C. 154(b) by 17 days.

(21) Appl. No.: 10/774,540

(22) Filed: Feb. 10, 2004

(65) Prior Publication Data

US 2004/0158129 A1    Aug. 12, 2004

(30) Foreign Application Priority Data

Feb. 10, 2003  (JP) ............................. 2003-031817
May 16, 2003  (JP) ............................. 2003-138099

(51) Int. Cl.
*A61B 1/06*  (2006.01)

(52) U.S. Cl. ................. 600/166; 600/111; 600/160; 600/165; 600/176; 348/45

(58) Field of Classification Search ............... 600/142, 600/160, 165–168, 175, 176, 129
See application file for complete search history.

(56) References Cited

U.S. PATENT DOCUMENTS

| | | | |
|---|---|---|---|
| 3,643,653 A * | 2/1972 | Takahashi et al. ........... 600/129 |
| 3,889,662 A * | 6/1975 | Mitsui ........................ 600/139 |
| 4,279,247 A * | 7/1981 | Kinoshita .................... 600/103 |
| 4,593,682 A * | 6/1986 | Heckele ....................... 600/139 |
| 4,790,295 A * | 12/1988 | Tashiro ........................ 600/176 |
| 5,120,953 A | 6/1992 | Harris |
| 5,193,525 A * | 3/1993 | Silverstein et al. .......... 600/125 |
| 5,323,009 A | 6/1994 | Harris |
| 5,846,185 A * | 12/1998 | Carollo et al. .............. 600/166 |
| 5,989,185 A * | 11/1999 | Miyazaki ..................... 600/175 |
| 6,066,090 A * | 5/2000 | Yoon .......................... 600/113 |
| 6,530,882 B1 * | 3/2003 | Farkas et al. ................ 600/168 |
| 2002/0099267 A1 * | 7/2002 | Wendlandt et al. .......... 600/173 |
| 2004/0122290 A1 * | 6/2004 | Irion et al. .................. 600/171 |

FOREIGN PATENT DOCUMENTS

JP        2000-121961        4/2000

* cited by examiner

*Primary Examiner*—Linda C. M. Dvorak
*Assistant Examiner*—Matthew J. Kasztejna
(74) *Attorney, Agent, or Firm*—Greenblum & Bernstein, P.L.C.

(57) ABSTRACT

An endoscope has an inserting tube to be inserted into a human body, first and second optical systems integrally secured to a tip end portion of the inserting tube. The first and second optical systems are for observing the in vivo tissues at different magnifications. A front end portion of the second optical system is protruded by a predetermined amount with respect to a front end portion of the first optical system so that the front end portion of said second optical system is located within a field of view of said second optical system.

19 Claims, 5 Drawing Sheets

ENDOSCOPE

BACKGROUND OF THE INVENTION

The present invention relates to endoscopes having optical systems.

An endoscope is generally provided with an observing optical system, which is used for observing in vivo tissues inside a human cavity. In particular, in an electronic endoscope, an objective optical system is provided as the observing optical system, and an image of a target portion (e.g., tissues in the human cavity) is formed on a solid state image capturing element such as a CCD (Charge Coupled Device).

Recently, a confocal probe, which employs principle of confocal micrography, has become widely known. The confocal probe is configured to illuminate in vivo tissues inside human cavity, and selectively receive light reflected by the tissues on an object side focal plane. The confocal probe is provided with a specific optical system (i.e., a confocal optical system) which has a relatively high magnification.

The confocal probe is typically inserted in an accessory channel of the endoscope, and is used to observe a minute object which cannot be observed using the normal observing optical system of the endoscope. The confocal probe is also used for obtaining an optical tomography of the in vivo tissues. An example of such a confocal probe is disclosed in Japanese Patent Provisional Publication No. P2000-121961A.

When an affected portion is found within the body during an inspection using the observing optical system of the endoscope which has relatively low magnification, the confocal probe is inserted through the accessory channel to obtain a high magnification image of the affected portion, which enables more precise inspection thereof.

In order to obtain the image of the affected portion using the confocal probe, the tip end of the confocal probe should be located precisely in front of the affected portion by manipulating the endoscope. However, it is difficult for the operator to know how much the tip end of the endoscope should be moved because of the following reasons.

Firstly, the magnification of the confocal probe is much higher than that of the normal observing optical system. Therefore, it is difficult for the operator to recognize whether the confocal probe is located at an intended position merely by comparing the images obtained by the low magnification optical system and the confocal optical system.

Secondly, since the confocal probe can freely slide along the accessory channel, the relative position of the confocal probe with respect to the low magnification optical system is not fixed, and the positional relationship between the areas observed by the low magnification optical system and the confocal probe is unknown.

Due to the above reasons, it is difficult for the operator to adjust the confocal probe at the right position for observing the affected portion, and a relatively long time is required for precise inspection using the confocal probe, which puts a burden upon a patient.

SUMMARY OF THE INVENTION

The present invention is advantageous in that an endoscope is provided, which includes two optical systems that have different magnifications, and a positional relationship between the areas observed using the two optical systems can be recognized without difficulties.

According to an aspect of the invention, there is provided an endoscope, which is provided with an inserting tube to be inserted into a human body, a first optical system secured in a tip end of the inserting tube for observing in vivo tissues within a human body at first magnification, and a second optical system secured in the tip end of the inserting tube for observing the in vivo tissues at second magnification that is higher than the first magnification.

In the endoscope arranged as describe above, an operator of the endoscope can easily recognize the positional relationship between the field of views of the first optical system and the second optical system since they are integrally mounted onto the flexible inserting tube.

Optionally, a portion of the second optical system may be located within the field of view of the first optical system.

With such a configuration, the operator of the endoscope can locate, with ease, the second optical system in front of a target, which is firstly found in the field of view of the first optical system, with viewing the position of the second optical system in the same field of view.

Further optionally, the endoscope may include a tip body mounted on a distal end of the inserting tube to hold the first optical system and the second optical systems at fixed positions.

Still optionally, the first optical system and the second optical system may be provided on an end surface of the tip body, and at least a front end portion of the second optical system is protruded with respect to the first optical system.

In this case, the first optical system may be arranged such that a front end portion is substantially flush with respect to the end surface of the tip body.

In some cases, an optical axis of the first optical system and an optical axis of the second optical system may be substantially parallel with each other.

In particular case, the second optical system is arranged not to interfere with a central area of the field of view of the first optical system.

Optionally, the end surface of the tip body may be formed with a protruded cover member that covers the side surface of the second optical system.

In this case, at least a part of the cover member may be observable in the field of view of the first optical system.

Further optionally, the part of the cover member does not interfere with a central area of the field of view of the first optical system.

Still optionally, the cover member of the tip body does not intersect a horizontal centerline and a vertical centerline of the field of view of the first optical system.

Furthermore, the cover member of the tip body may surround at least a part of a circumferential surface of the end portion of the second optical system.

In a particular case, the tip body may be made of hard resin.

Further, an outer surface of the cover member of the tip body may be tapered.

Still optionally, the tip body may be formed with an outlet of a forceps channel for introducing a forceps into the human body. In this case, the cover member of the tip body may be formed not to interfere with the forceps protruded from the outlet.

In a particular case, the second optical system is a confocal optical system.

Optionally, the endoscope may include an imaging device provided in the tip end of the inserting tube, and
the first optical system may form an image of a target on the imaging device.

Further optionally, the endoscope may include an optical fiber that transmits light returned from the in vivo tissues. The second optical system may be arranged such that only the light from a level of a focal plane of the second optical system is transmitted through the optical fiber.

According to another aspect of the invention, there is provided an endoscope, which includes an inserting tube to be inserted into a human body, a first optical system secured in a tip end of the inserting tube for observing in vivo tissues within a human body at first magnification, and a second optical system secured in the tip end of the inserting tube for observing the in vivo tissues at second magnification that is higher than the first magnification. With this configuration, a front end portion of the second optical system is protruded by a predetermined amount with respect to a front end portion of the first optical system.

According to a further aspect of the invention, there is provided an endoscope, which is provided with an inserting tube to be inserted into a human body, a first optical system secured in a tip end of the flexible inserting tube for observing in vivo tissues within a human body at first magnification, and a second optical system secured in the tip end of the flexible inserting tube for observing the in vivo tissues at second magnification that is higher than the first magnification. With this configuration, the first optical system and the second optical system are arranged such that a front end portion of the second optical system is within a field of view of the first optical system.

BRIEF DESCRIPTION OF THE ACCOMPANYING DRAWINGS

FIG. 1 schematically shows an electronic endoscope system according to an embodiment of the invention;

DETAILED DESCRIPTION OF THE EMBODIMENTS

Hereinafter, an embodiment of the present invention will be described with reference to the accompanying drawings.

Figure 1:
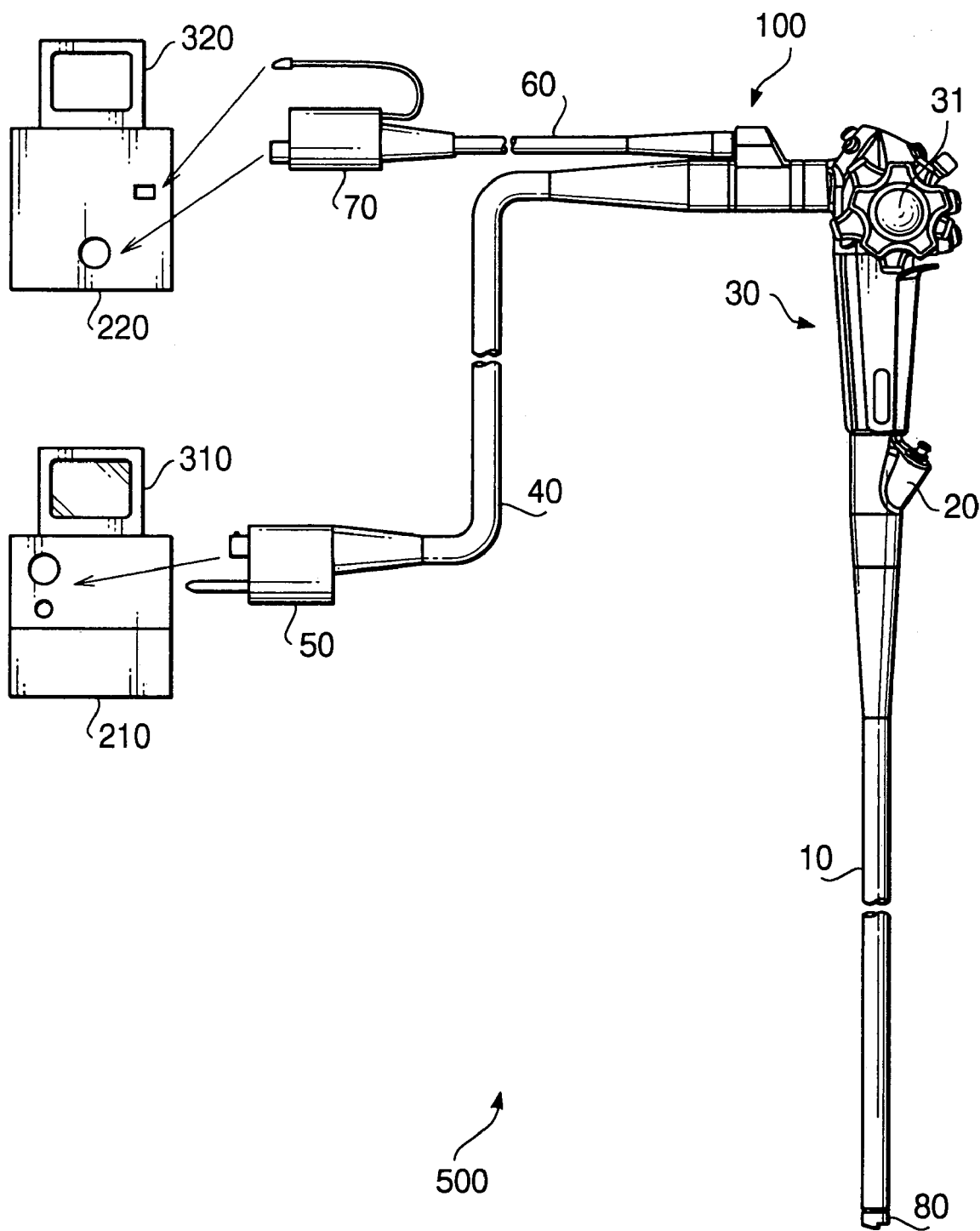

FIG. 1 schematically shows an electronic endoscope system 500 according to the embodiment of the invention. The electronic endoscope system 500 includes an electronic endoscope 100, a first processor 210, a second processor 220, a first monitor 310 and a second monitor 320. As will be describe later, the electronic endoscope 100 includes a first optical system for observing in vivo tissues inside the human body at a low magnification and a second optical system for observing the in vivo tissues at a high magnification. The first processor 210 processes and displays the low magnification image on the first monitor 310. The second processor 220 processes and displays the high magnification image on the second monitor 320.

The electronic endoscope 100 includes a flexible inserting tube 10, which is to be inserted into a human body, and an operation portion 30 fixed on a proximal end of the flexible inserting tube 10.

The electronic endoscope 100 further includes a universal cord 40 and a confocal system cord 60, both extending from the operating portion 30. The universal cord 40 is connected with the first processor 210 through an endoscope connector 50 provided on the end of the universal cord 40. The confocal system cord 60 is connected with the second processor 220 through a confocal system connector 70 provided on the end of the confocal system cord 60.

A forceps inserting opening 20 is formed on the operation portion 30 near the distal end thereof. The forceps inserting opening 20 is for inserting a forceps into the flexible inserting tube 10. Various kinds of forceps for stopping bleeding, picking up in vivo tissues, or the like are selected in accordance with the type of operation to be performed, and is inserted in the flexible inserting tube 10 through the forceps inserting opening 20. The forceps is advanced along a forceps channel (not shown) formed through the flexible inserting tube 10 and protrudes from the tip end 80 of flexible inserting tube 10.

The operating portion 30 is provided with multiple knobs 31, which are manipulated for controlling bending direction and angle of the flexible inserting tube 10 to observe a desired portion inside the human body with the electronic endoscope 100 or to treat them with the forceps.

Figure 2:
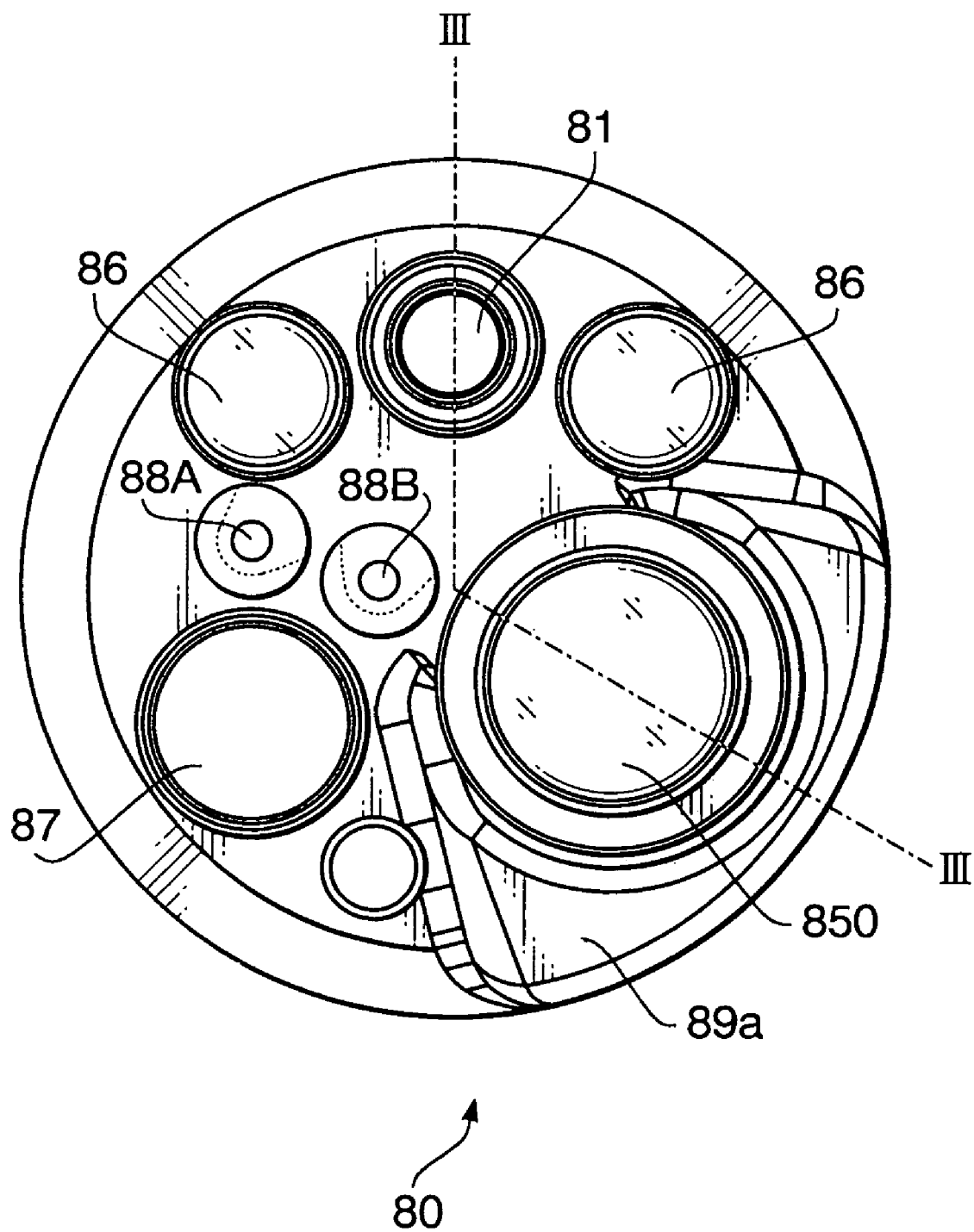
FIG. 2 is a front view of a tip end of a flexible inserting tube of an electronic endoscope shown in FIG. 1.
Figure 3:
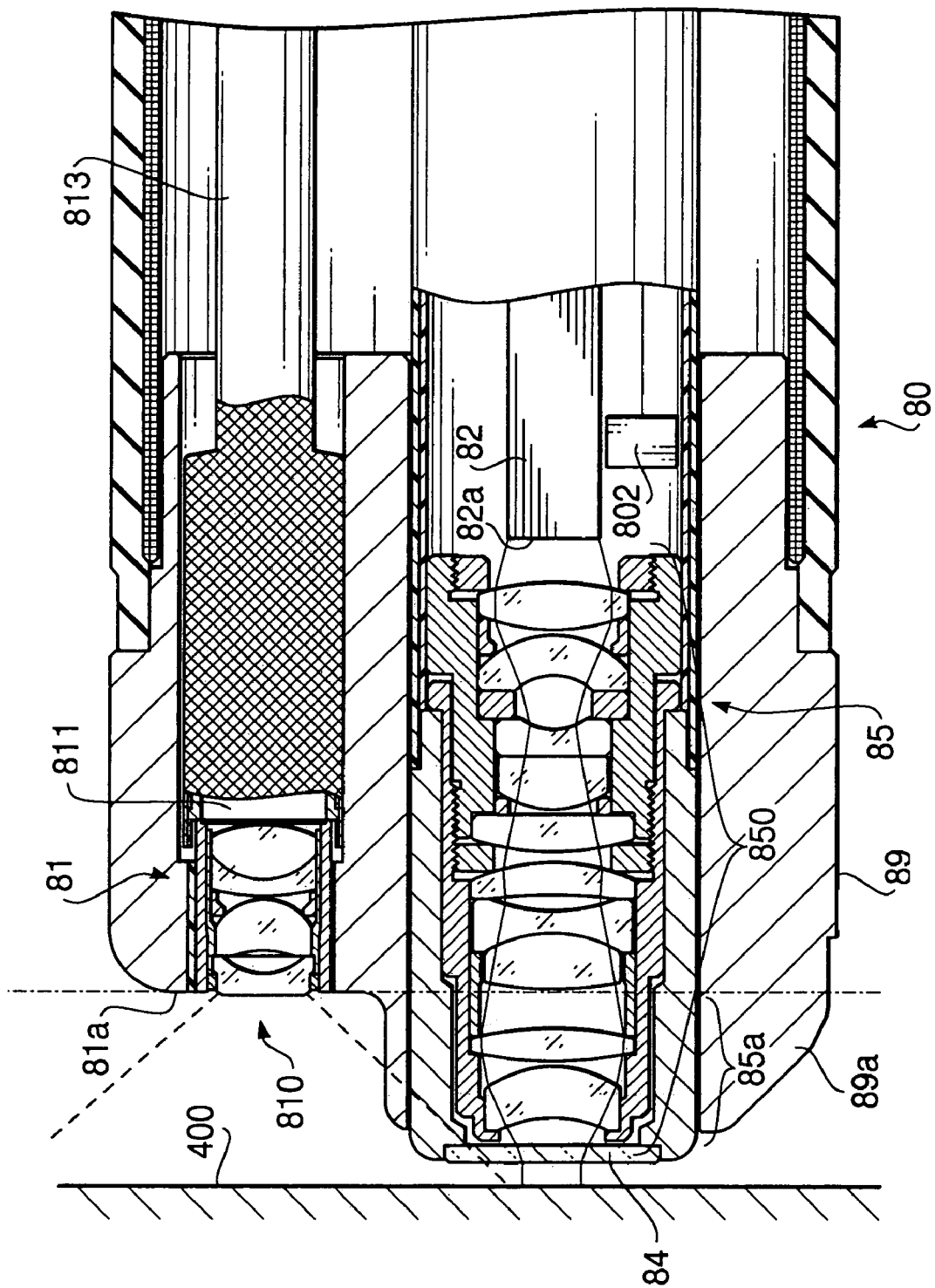
FIG. 3 is a sectional view of the tip end of the flexible inserting tube shown in FIG. 2 taken along line III-III.

FIG. 2 is a front view of the tip end 80 of the flexible inserting tube 10, and FIG. 3 is a sectional view of the tip end 80 taken along a line III-III in FIG. 2.

A tip body 89, made of hard resin, for example, is fixed on the tip end 80 of the flexible inserting tube 10. The front face 81a of the tip body 89 is provided with two illumination windows 86 (see FIG. 2) through which light is emitted onto a target (e.g., tissues to be observed) 400, a forceps channel opening 87 through which the forceps is protruded, and an air feeding opening 88A and a water feeding opening 88B for feeding air and water to the target 400, respectively.

As shown in FIG. 3, the tip body 89 holds an endoscope unit 81 and a confocal unit 85. The endoscope unit 81 includes an objective lens system (the first objective lens system) 810 for observing the target 400 in the human body at a low magnification and a solid-state imaging device 811. The solid-state imaging device 811 is disposed on a rear focal plane of the objective lens system 810. Thus, the objective optical system 810 forms an image of the target 400 on the solid-state imaging device 811.

The confocal unit 85 includes an optical fiber 82 and an objective lens system (the second objective lens system) 850 for observing the target 400 at a high magnification. The second objective lens system 850 has a glass cover 84 at the front end thereof for protecting other optical elements of the second objective lens system 850. The confocal unit 85 holds an optical fiber 82 so that a distal end face 82a thereof is on a rear focal plane of the second objective lens system 850. The optical fiber 82 is a single mode optical fiber connected to the confocal system cord 60 that is connected to the second processor 220 with the confocal system connector 70. The optical fiber 82 extends from the tip end 80, through the flexible inserting tube 10 and the operation portion 30.

The confocal unit 85 further includes an actuator 802, such as a piezoelectric actuator, for moving the distal end face 82a of the optical fiber 82. As will be described later, a laser beam is emitted from the distal end face 82a of the optical fiber 82 and irradiated on the target 400 through the second optical system 850. The actuator 802 swings the distal end face 82a of the optical fiber 82 so that the laser beam scans on the target 400.

Referring back to FIG. 1, the first processor 210 is provided with a not shown light source. The light emitted from the light source is transmitted through two light guides (not shown) extending through the electronic endoscope 100 (i.e., the universal cord 40, the operation portion 30, and the flexible inserting tube 10) and emitted from the illumination windows 86 to illuminate the target 400.

The first optical system 810 forms an image of the illuminated target 400 on the solid-state imaging device 811. The solid-state imaging device 811 converts the optical image into an image signal and sends it to the first processor 210 through a signal line 813 (see FIG. 3) extending through the electronic endoscope 100 (i.e., the flexible inserting tube 10, the operation portion 30, and the universal cord 40). The first processor 210 receives the image signal and generates a video signal, which is sent to the first monitor 310 to display the low magnification image captured by the solid-state imaging device 811.

The second processor 220 is provided with a not shown laser source. The laser beam emitted from the laser source is introduced into the optical fiber 82 of the electronic endoscope 100 through the confocal system connector 70. The laser beam transmits through the optical fiber 82 and emerges from the distal end face 82a thereof to proceed toward the second optical system 850.

The second optical system 850 focuses the light to a small spot on the target 400, which is located on the front focal plane of the second optical system 850. Light returned from the illuminated spot on the target 400 is collected by the second objective optical system 850 and converged onto the distal end face 82a of the optical fiber 82. The light returned from the illuminated spot on the target 400 can be either reflected light or fluorescence light emanating from the tissues.

As previously described, the distal end face 82a of the optical fiber 82 is located on the rear focal plane of the second optical system 850. Thus, the distal end face 82a is conjugate to the illuminated spot on the target 400 with respect to the second objective optical system 850. Since the core of the optical fiber 82 is quite small, the core serves as a confocal pin hole, which allows only the light from the spot on the target 400 to enter the optical fiber 82 and to block light that did not originate from the spot. Thus, the second objective lens system 850 converges light from the target 400 at a level of the front focal plane thereof on a distal end face 82a of the optical fiber 82.

The returned light introduced into the optical fiber 82 transmits therethrough to the second processor 220. The second processor 220 includes a not shown photosensor, which detects the intensity of the light transmitted through the optical fiber 82.

As previously described, the distal end of the optical fiber 82 is moved by the actuator 802 so that the laser beam scans the target 400. Since the optical characteristic of the target 400, which is in vivo tissues in the present embodiment, varies with the location thereon, the intensity of the light reflected by the target 400 varies as the laser beam is scanned. Thus, the second processor 220 can generate an optical tomography of the target 400 based on the intensity of the light received through the optical fiber 82. The optical tomography is then displayed on the second monitor 310.

Next, a positional relationship between the endoscope unit 81 and the confocal unit 85 will be described with reference to FIGS. 2 and 3. As previously described, the tip body 89 is mounted on the tip end 80 of the flexible inserting tube 10. The endoscope unit 81 is held by the tip body 89 such that the front face of the first optical system 810 is substantially flush with the front face 81a of the tip body 89. The confocal unit 85 is disposed such that a front end portion 85a thereof protrudes from the front face 81a of the tip body 89. In other words, the confocal unit 85 is disposed such that the second optical system 850 is slightly protruded forward with respect to the first optical system 810.

Figure 4:
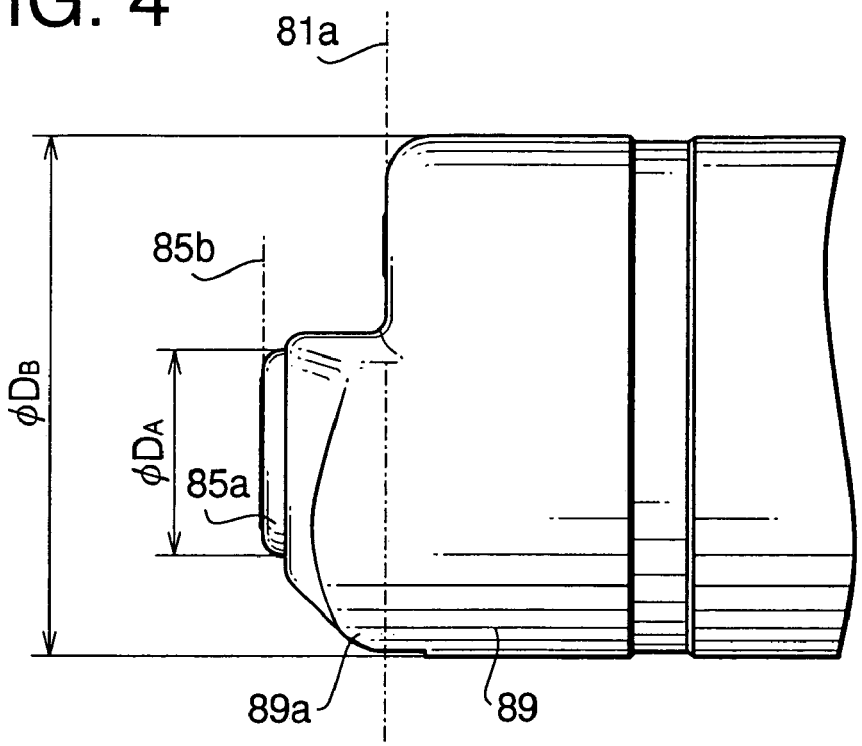
FIG. 4 shows a side view of a tip end of the flexible inserting tube shown in FIG. 2.

FIG. 4 is a side view of the tip end 80 of the flexible inserting tube 10. As shown in FIG. 4, the tip body 89 has a diameter of $\phi D_B$, in which the first objective lens system 810 and the second objective lens system 850 are held. The confocal unit 85 includes a barrel member in which the optical elements of the second optical system 850 are secured. The front end portion 85a of the second objective lens system 850 (i.e., the barrel member) has a diameter of $\phi D_A$, which is smaller than $\phi D_B$, as shown in FIG. 4, and is protruded forward with respect to the front face 81a of the tip body 89.

When the tip end 80 of the inserting tube 10 is moved toward the target 400, the front face 85b of the front end portion 85a contacts the target 400. At this stage, the front face 81a of the tip body 89 does not contact the target 400 due to the protruded structure of the confocal unit 85. Since the positional relationship of the second objective lens unit 850 with respect to the electronic endoscope 100 is fixed, the user can have the confocal unit 85 (i.e., the front face of the second objective lens unit 850, or the protruded portion 85a) contact the target 400 stably.

Further to the above, because of the protruded structure of confocal unit 85, only in a small area, the front face 85b of the confocal unit 85 contacts the target 400. If the front face 85b is flush with the front face 81a and the tip end 80 is to be contact the target, in a relatively wide area (whose diameter is $\phi D_B$), the front face 81a of the tip body 89 should contacted the target 400. In such a case, the front face 81a may easily incline with respect to the surface of the target 400. That is, in such a case, a surface contact between the front face 81a and the target 400 will be difficult to be achieved. According to the embodiment, however, only the front face 85b of the protruded portion 85a of the confocal unit 85 contacts the target 400. Therefore, it is ensured that the front face 85b closely contact the surface of the target 400.

Further to the above, since the first lens unit 810 is located on the operation portion side of the endoscope 100 with respect to the second lens unit 850, an insertion length of the tip body having the diameter of $\phi D_B$ can be reduced. The reduced amount is compensated by the portion of the tip body 89 having a smaller diameter (i.e., the protruded portion 85a). As described above, the tip body 89 is made of hard resin. Therefore, by forming the tip portion to have a smaller diameter than the rear portion (whose diameter is $\phi D_B$), load to a patient can be well reduced.

The front face 81a of the tip body 89 is partially protruded to form a cover portion 89a that surrounds the circumferential surface of the front end portion 85a of the confocal unit 85. The cover portion 89a protects the front end portion 85a of the confocal unit 85, which is thin and week, so that a large force will not be applied thereto directly.

The cover portion 89a is tapered toward the front end thereof. Thus, the cover portion 89a, which protrudes from the front face 81a of the tip end 80, does not cause damage to a body even when the flexible inserting tube 10 is inserted into a narrow space of the body.

Figure 5:
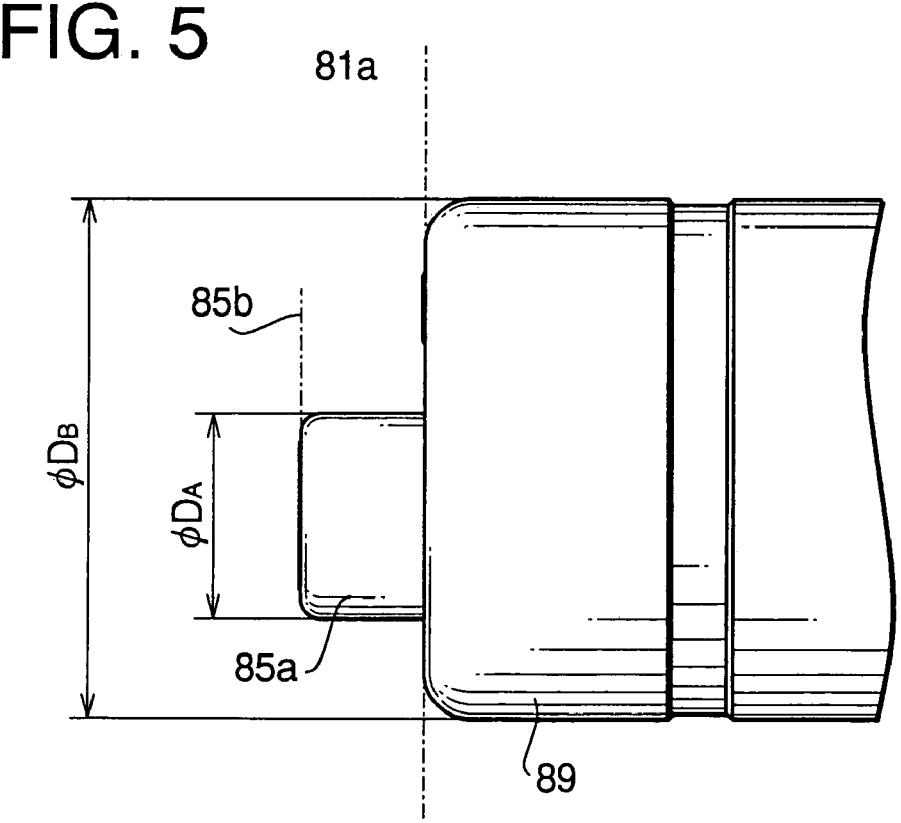
FIG. 5 shows a side view of a tip end according to a modification of the embodiment.

FIG. 5 shows a side view of the tip end 80 according to a modification of the embodiment. In this example, The cover portion 89a is not provided, and only the front end portion 85a of the second objective lens unit 850 is protruded with respect to the front face 81a of the tip body 89. Also in this case, since the tip end portion 85a of the tip body 89 has a smaller diameter (i.e., $\phi D_A$) than the rear portion (whose diameter is $\phi D_B$), load to a patient can be reduced.

Figure 6A:
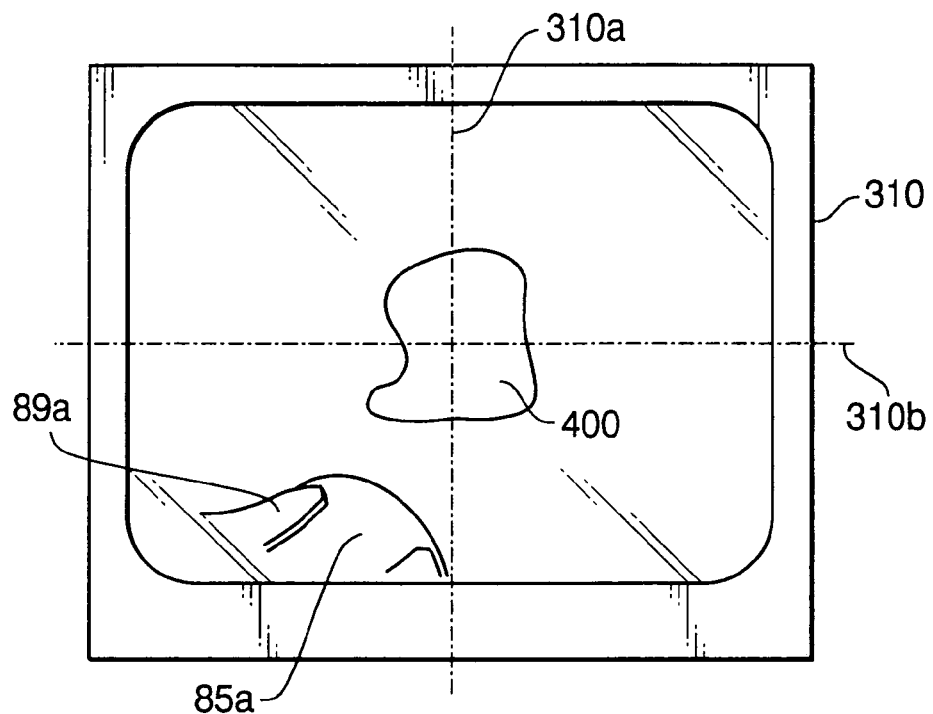
FIGS. 6A and 6B show images displayed on a monitor of the electronic endoscope system shown in FIG. 1.
Figure 6B:
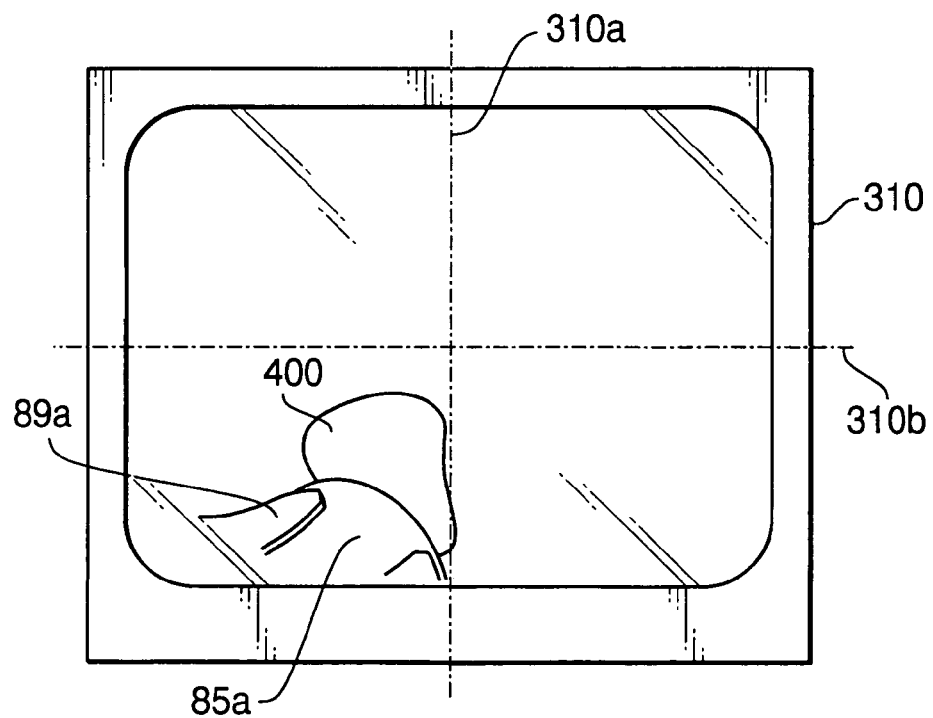

FIGS. 6A and 6B show the first monitor 310 displaying the image captured through the first optical system 81. The confocal unit 85 and the cover portion 89a of the tip body 89 are arranged such that they are partially located within the image displayed on the first monitor 310, or within the view filed of the first optical system 81. The confocal unit 85 and the cover portion 89a of the tip body 89 are also arranged such that they do not interfere with the central area of the image displayed on the first monitor 310, which is the most suitable area for observation. Specifically, the confocal unit 85 and the cover portion 89a of the tip body 89 are arranged such that they do not intersect a horizontal center line 310a and a vertical center line 310b defined on the screen of the first monitor 310 (or the view field of the first optical system 81). The arrangement described above allows the operator to observe the target 400 at the center of the screen of the first monitor 310, while confirming the position of the confocal unit 85 at the peripheral of the screen.

It should be noted that the confocal unit 85 is also located apart enough from the forceps channel opening 87 to prevent it from interfering with the operation of the forceps protruding from forceps channel opening 87.

Next, an exemplary way of observing in vivo tissues with use of the electronic endoscope 100 will be described. First, a low magnification image of the target 400, which is obtained using the first optical system 810, is displayed on the first monitor 310. The operator observes the target 400 at the central area of the screen of the first monitor 310 while confirming the position of the confocal unit 85 at the peripheral of the screen, as shown in FIG. 6A. This allows the operator to easily determine the positional relationship between the target 400 and the area that can be observed through the confocal unit 85.

When the target 400 should be observed at a high magnification, the operator manipulates the electronic endoscope 100 so that the target 400 is located in front of the confocal unit 85, as shown in FIG. 6B. When the target 400 is located in front of the confocal unit 85, a high magnification image of the target 400 is obtained through the confocal unit 85 and displayed on the second monitor 320. The high magnification image allows the operator to inspect the target 400 in detail.

It should be noted that, since the relative position of the target 400 to the confocal unit 85 can be confirmed in the first monitor 310 simultaneously, the operator can locate the target 400 in front of the confocal unit 85 quickly and precisely, which reduces the time required for endoscopic inspection and operation.

The present disclosure relates to the subject matters contained in Japanese Patent Applications No. P2003-031817, filed on Feb. 10, 2003 and No. P2003-138099, filed on May 16, 2003 which are expressly incorporated herein by reference in their entireties.

What is claimed is:

1. An endoscope comprising: an inserting tube to be inserted into a human body; a first optical system fixed in a tip end of said inserting tube for observing in vivo tissues within a human body at a first magnification; a second optical system fixed in the tip end of said inserting tube for observing the in vivo tissues at a second magnification that is higher than the first magnification; and a tip body mounted on a distal end of said inserting tube, said tip body holding said first optical system and said second optical system, wherein a portion of said second optical system is within the field of view of said first optical system, and wherein a position of said first optical system is fixed in relation to a position of said second optical system within a single inserting tube.

2. The endoscope according to claim 1, wherein said second optical system is a confocal optical system.

3. The endoscope according to claim 2, further comprising:
an imaging device provided in said tip end of said inserting tube, and
wherein said first optical system forms an image of a target on said imaging device.

4. The endoscope according to claim 2, further comprising an optical fiber that transmits light returned from the in vivo tissues, only the light from a level of a focal plane of said second optical system being transmitted through said optical fiber.

5. An endoscope comprising:
an inserting tube to be inserted into a human body;
a first optical system fixed in a tip end of said inserting tube for observing in vivo tissues within a human body at a first magnification; and
a second optical system fixed in the tip end of said inserting tube for observing the in vivo tissues at a second magnification that is higher than the first magnification,
wherein said first optical system and said second optical system are provided on an end surface of a tip body mounted on a distal end of said inserting tube, said second optical system being arranged such that at least a front end portion thereof is protruded with respect to said first optical system, and
wherein a position of said first optical system is fixed in relation to a position of said second optical system within a single inserting tube.

6. The endoscope according to claim 5, wherein said first optical system is arranged such that a front end portion thereof is substantially flush with respect to the end surface of said tip body.

7. The endoscope according to claim 6, wherein an optical axis of said first optical system and an optical axis of said second optical system are substantially parallel with each other.

8. The endoscope according to claim 6, wherein said second optical system is arranged not to interfere with a central area of the field of view of said first optical system.

9. The endoscope according to claim 5,
wherein said tip body is formed with an outlet of a forceps channel for introducing a forceps into the human body, and
wherein a cover member of said tip body is formed not to interfere with the forceps protruded from said outlet.

10. The endoscope according to claim 5, wherein said second optical system is a confocal optical system.

11. The endoscope according to claim 10, further comprising:
an imaging device provided in said tip end of said inserting tube,
wherein said first optical system forms an image of a target on said imaging device.

12. The endoscope according to claim 10, further comprising:
an optical fiber that transmits light returned from the in vivo tissues, only the light from a level of a focal plane of said second optical system being transmitted through said optical fiber.

13. An endoscope comprising:
an inserting tube to be inserted into a human body;
a first optical system fixed in a tip end of said inserting tube for observing in vivo tissues within a human body at a first magnification; and
a second optical system fixed in the tip end of said inserting tube for observing the in vivo tissues at a second magnification that is higher than the first magnification,
wherein said first optical system and said second optical system are provided on an end surface of a tip body mounted on a distal end of said inserting tube, said second optical system being arranged such that at least a front end portion thereof is protruded with respect to said first optical system,
wherein the end surface of said tip body is formed with a protruded cover member that covers side surface of said second optical system.

14. The endoscope according to claim 13, wherein at least a part of said cover member is observable in the field of view of said first optical system.

15. The endoscope according to claim 14, wherein said tip body is arranged such that said at least a part of said cover member does not interfere with a central area of the field of view of said first optical system.

16. The endoscope according to claim 15, wherein said tip body is arranged such that said cover member of said tip body does not intersect a horizontal centerline and a vertical centerline of the field of view of said first optical system.

17. The endoscope according to claim 13, wherein said cover member of said tip body surrounds at least a part of a circumferential surface of the end portion of said second optical system.

18. The endoscope according to claim 17, wherein said tip body is made of hard resin.

19. The endoscope according to claim 17, wherein an outer surface of said cover member of said tip body is tapered.

* * * * *